(12) United States Patent
Murphy

(10) Patent No.: US 9,293,026 B2
(45) Date of Patent: *Mar. 22, 2016

(54) BED EXIT NIGHT LIGHT WITH INCREASED FUNCTIONALITY

(71) Applicant: Daniel R. Murphy, Grandview, TX (US)

(72) Inventor: Daniel R. Murphy, Grandview, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/324,912

(22) Filed: Jul. 7, 2014

(65) Prior Publication Data

US 2016/0005288 A1 Jan. 7, 2016

Related U.S. Application Data

(63) Continuation of application No. 13/598,568, filed on Aug. 29, 2012, now Pat. No. 8,810,379.

(51) Int. Cl.
| | |
|---|---|
| G08B 23/00 | (2006.01) |
| G08B 5/22 | (2006.01) |
| G08B 21/00 | (2006.01) |
| H01H 35/00 | (2006.01) |
| G01L 7/00 | (2006.01) |
| G08B 21/04 | (2006.01) |
| H05B 37/02 | (2006.01) |
| F21V 23/04 | (2006.01) |
| A61B 5/11 | (2006.01) |
| F21W 131/208 | (2006.01) |

(52) U.S. Cl.
CPC .......... *G08B 21/0461* (2013.01); *A61B 5/1115* (2013.01); *F21V 23/0442* (2013.01); *H05B 37/0227* (2013.01); *F21W 2131/208* (2013.01)

(58) Field of Classification Search
CPC .......................................................... A47B 7/00
See application file for complete search history.

(56) References Cited

U.S. PATENT DOCUMENTS

| | | | |
|---|---|---|---|
| 8,810,379 B2 * | 8/2014 | Murphy | 340/286.07 |
| 2007/0136102 A1 * | 6/2007 | Rodgers | 705/3 |
| 2007/0171046 A1 * | 7/2007 | Diem | 340/539.13 |
| 2009/0091458 A1 * | 4/2009 | Deutsch | 340/573.1 |
| 2009/0119843 A1 * | 5/2009 | Rodgers et al. | 5/611 |
| 2011/0133655 A1 * | 6/2011 | Recker et al. | 315/159 |
| 2012/0025991 A1 * | 2/2012 | O'Keefe | A61B 5/1115 340/573.4 |
| 2014/0327545 A1 * | 11/2014 | Bolling et al. | 340/573.1 |

* cited by examiner

*Primary Examiner* — Jennifer Mehmood
*Assistant Examiner* — Pameshanand Mahase
(74) *Attorney, Agent, or Firm* — Norred Law, PLLC; Warren V. Norred

(57) ABSTRACT

The invention is an improved Bed Exit Night Light System designed to illuminate a hospital room if a patient leaves his bed, but automatically tracks medical personnel movement within the room and illuminates the room as appropriate to the medical tasks taking place.

16 Claims, 4 Drawing Sheets

BED EXIT NIGHT LIGHT WITH INCREASED FUNCTIONALITY

CROSS-REFERENCES TO RELATED APPLICATIONS

This application is a continuation-in-part of U.S. patent application Ser. No. 13/598,568, filed Aug. 29, 2012 to Daniel Murphy, which is incorporated fully herein. Much of the content of this application comes directly from this former patent for context, but the absence of any content from the former patent in this application should not be interpreted to mean that the content is not incorporated.

STATEMENT REGARDING FEDERALLY SPONSORED RESEARCH AND DEVELOPMENT

None.

THE NAMES OF THE PARTIES TO A JOINT RESEARCH AGREEMENT

None.

INCORPORATION-BY-REFERENCE OF MATERIAL SUBMITTED ON A COMPACT DISC

None.

BACKGROUND OF THE INVENTION

1. Field of the Invention

The invention concerns hospital bedroom lighting.

2. Background Art

Hospitalized patients often struggle when they waken in unfamiliar rooms, and can hurt themselves by attempting to navigate in the dark. The industry has a variety of lighting systems to handle this challenge, none of which provide a satisfactory solution.

U.S. Pat. No. 6,234,642 discloses a solution in which a lighting system is added to a bed's undercarriage, that illuminates the area around the edge of the bed. The lighting function of this product is designed for use primarily in multi-bed hospital patient rooms, and therefore the light only illuminates the area under the edge of the bed, so as not to disturb other patients in the MOM.

The dim, narrowly focused light does not illuminate enough of the room to allow the patient to safely navigate their way to and from the restroom at night, which is how and why most patient falls within a hospital occur. Moreover, a hospital must buy the specific bed model that has the lights installed in order to gain the benefit of the light associated with the bed. There is no capability to use this product to retrofit existing beds.

U.S. Pat. No. 5,600,305 discloses a bed-exit sensing system that employs an infrared sensor been that sits low near the bed and parallel to the bedside to detect a patient leaving the bed.

This system has many problems. Modern hospital beds that have integral bed exit-sensing have made this system obsolete. Since a patient could potentially exit the bed from either side, it appears that two of the systems would be necessary, or at least the system would have to be changed from one side to the other.

This system also is duplicative of modern hospital beds, which tend to have an integral patient-detection signal that can be used for any purpose, and makes the signal system irrelevant. And finally, the IR beam will be interrupted as hospital staff move within the room and equipment is moved within the room, as electric cables and signal wires are repositioned. This movement will create false positive signals of patient movement. Movement of equipment will cause the system sensors to require frequent realignment.

The system does have a light that is mounted to the "Master Unit" that, according to the Abstract, sits on the patient floor, but with all of the false alarms that this system is bound to generate, the light would be on almost constantly and if bright enough to be effective, would keep the patient awake.

U.S. Pat. No. 5,471,198—This patent discloses a bed-mountable system that senses the presence or absence of a patient by using a reflected electromagnetic beam. It includes an output relay that "may alternatively operate an alarm bell or light to indicate the absence of the patient". In this case, the implication is that the "light" is intended to be an indicator light to alert staff, similar to the way a nurse call corridor light indicates an active call. It does not, in and of itself, include any kind of lighting to illuminate the patient room.

The ability to detect the presence of a patient in a hospital bed has been perfected by bed manufacturers. This patent is still valid, but irrelevant to today's hospital beds, which routinely come with patient detection systems.

U.S. Pat. No. 4,067,005—This patent discloses a "patient exit" signal, in which pressure sensors are mounted to the bed side rails. The signals are intended to detect when the patient is attempting to exit the bed and "sound a buzzer, and/or a call bell, and/or illuminate the bed so that a nurse or attendant is amply alerted . . . "

Once again, as in above patents and current products, the purpose is to illuminate only the bed itself to alert staff. It is not intended to illuminate the room. Other obvious problems are that the patient may accidently set the system off by grabbing the side rail when they are attempting to simply change their position in the bed; visitor and staff may set it off by leaning over the side rail to tend to the patient or lower it. Multiple false alarms tend to cause the staff to ignore all alarms.

U.S. patent application Ser. No. 13/598,568, filed previously by the inventor, has previously received a notice of allowance for a bed monitoring system which delays patient monitoring until after giving a patient some time to become settled in the bed. However, this patent does not provide for integration with patient locating system and bed-to-nurse call interfaces and wireless paging and phone systems.

Another challenge for the industry is the monitoring of what kind of staff has entered a hospital bed room, and providing lighting sufficient for that type of staff. When room lights come on, these systems do not distinguish between the likely lighting need of the entering staff member. When a doctor comes in, he may well need the light to be fully on, but a nurse performing mundane status checks may need minimal lighting. A lighting system should distinguish and provide lighting appropriate for the task at hand.

These patents summarize the prior art, which focuses on ways of detecting the presence of patients in beds, a task easily handled by modern hospital beds. The hospital bed industry needs a system that will assist hospitalized patients by lighting rooms only when patients leave their beds, does not light the room unduly by activating without false positives and does not create a need for hospital staff to modify their everyday operations to maintain the system.

BRIEF SUMMARY OF THE INVENTION

The invention shown in FIG. 1 is a Bed Exit Night Light System designed to illuminate a hospital room if a patient leaves his bed, but is not necessarily activated by the presence of hospital staff or casual movement of equipment. This invention was earlier disclosed by U.S. patent application Ser. No. 13/598,568, filed Aug. 29, 2012 to Daniel Murphy. This continuation-in-part application adds additional disclosure of optional monitoring and lighting control elements which will lighten a dark hospital room by an amount determined in accordance with medical staff who have entered the room.

The system is based on a Control Unit 11 that monitors the Bed Sensor 13 and the presence of medical staff through RFID Tags 21 and a Transponder 25 to control the room lighting, energizing the Room Light 15 when a patient leaves the bed, and keeping the Room Light 15 on until deactivated by the patient or hospital staff.

BRIEF DESCRIPTION OF THE SEVERAL VIEWS OF THE DRAWING(S)

DETAILED DESCRIPTION OF THE INVENTION

The invention described herein builds upon existing components of modern hospital beds, adding a Control Unit 11, a Bed Sensor 13, Transponder 25 and a badge system with RFID Tags 21 for medical staff. The invention is active when a patient's room lighting is not operating, turning on Room Light 15 when a patient gets out of bed, or when medical personnel enter the room wearing a badge equipped with an RFID Tag 21 which tells the Control Unit 11 to raise the lighting by some pre-programmed level appropriate for the medical tasks to be performed.

In an alternate configuration, the invention only functions when the room is dark. In practice, the invention comprises the Control Unit 11 and new wiring connections that employ the additional components.

Figure 1:
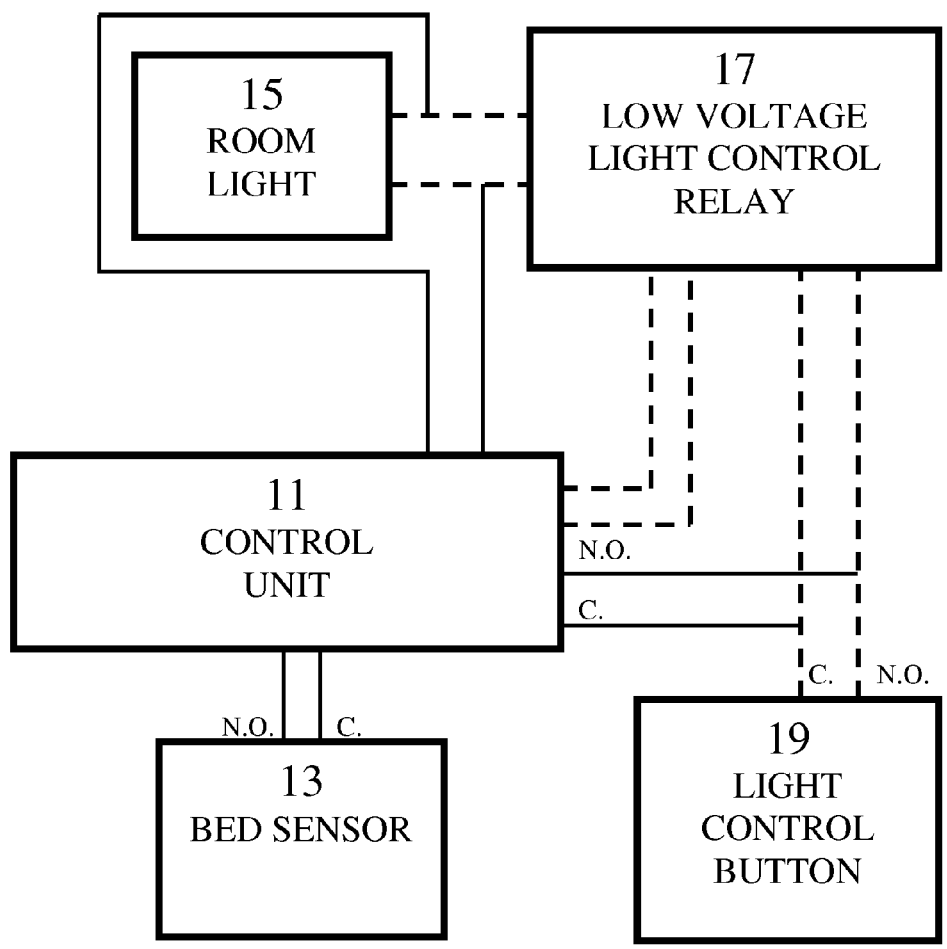
FIG. 1 is a block diagram of one embodiment of the invention.

FIG. 1 shows a control diagram showing the physical connection between the various components of the invention. This diagram assumes that the Low Voltage Control Relay (LVCR) 17 changes state each time its inputs show a closed contact, just as the Light Control Button 19 momentarily closes its normally open contacts to change the state of the LVCR 17. The dotted lines indicate connections that already exist in typical circumstances.

The embodiment shown in FIG. 1 assumes that the Control Unit 11 senses the Room Light 15 operation by monitoring the voltage source across the Room Light 15. Alternatively, the Control Unit could have a light detector which eliminates that direct wired connection.

Figure 2:
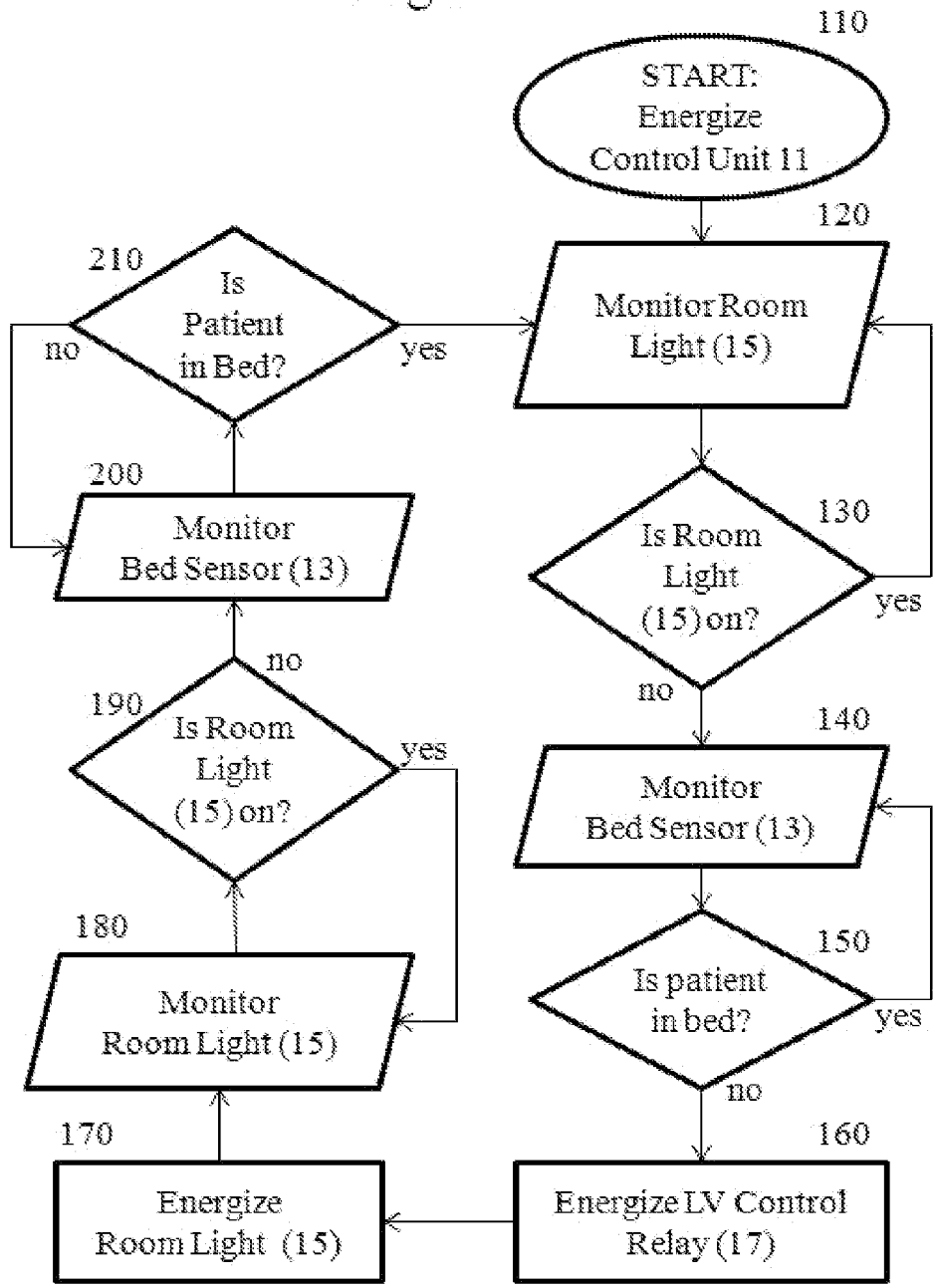
FIG. 2 is a flow chart for the embodiment of the invention's operation shown in FIG. 1.

As shown in FIG. 2, the operation begins when a user activates the system, usually by a button on the Control Unit 11 (Step 110). After activation, the Control Unit 11 begins to monitor the room's overhead light (Step 120). The Control Unit does nothing unless the Room Light 15 is off (Step 130).

When the Room Light 15 is off, the Control Unit 11 monitors the Bed Sensor 13 to determine if a patient is present (Step 140). The Bed Sensor 13 is usually a "normally open" (NO) contact that closes when a patient leaves the bed; this apparatus is included in most modern hospital beds. When a patient leaves the bed, the Bed Sensor 13 changes state, informing the Control Unit 11 of the patient's activity. (Step 150).

The Control Unit can also function with a Bed Sensor 13 that is a "normally closed" (NC) contact here as well; the invention just needs to take into account the status of the contact when a patient is in the bed, and that the status changes when a patient leaves the bed.

When the Control Unit 11 is informed by the Bed Sensor 13 that a patient has left the monitored hospital bed, the Control Unit 11 activates the Low-Voltage Control Relay (LVCR) 17 that most modern hospitals use to operate the Room Light 15 (Step 160).

When activated, the LVCR 17 energizes the Room Light 15 (Step 170). The Control Unit 11 ceases activity while monitoring Room Light 15 (Step 180). The Control Unit 11 monitors the Room Light 15 until de-energized by an outside actor (Step 190).

The Control Unit 11 then monitors the Bed Sensor 13 (Step 200). Once the Room Light 15 is off, and the patient is back in bed, the Control Unit 11 repeats the cycle (Step 210). Alternatively, a timer can also be employed to give a patient time to settle himself before beginning to monitor movement of the patient and avoid false positives.

In this improved lighting system, an optional Manual Override Switch 29 can be added which stops all operation and allows the conventional light switch operation in the hospital room. However, none of the apparatus discussed or shown prevents a user from turning on the existing light control. The Control Unit 11 triggers the LVCR 17 by emulating the Light Control Button 19 by sending it a closed contact to its inputs.

As shown in FIG. 2, the Control Unit 11 turns the Room Light 15 on when a patient gets out of his bed and the Room Light 15 is off, and remains on until the patient or nursing staff turns the light back off. Once the Room Light 15 is on, the Control Unit 11 ignores further input until a patient or one of the hospital staff deactivates the Room Light 15 by using Light Control 19, typically a momentary switch to turn the Room Light 15 off. Then the Control Unit 11 waits until the patient is back in bed and the light is off before starting the monitoring cycle anew.

When the existing Room Light 15 illuminates the room, the patient is brought to a more awakened state when they try to exit the bed and they are able to see all of the potential tripping obstacles in their path, thereby reducing the likelihood of a patient fall.

In typical use, the Control Unit 11 is a permanently-mounted device that is located above the ceiling, but could be mounted anywhere on the patient room head wall, under the bed, or any other out-of-the-way location. Unlike previous solutions to this challenging situation, it is not disturbed by staff or equipment as it is moved around in the patient's room.

Since modern patient beds can sense the patient's weight and only trigger the bed exit alert when the patient's weight is lifted, false alarms are kept to a minimum.

The Control Unit 11 also has a contact closure output that could then be used to trigger the nurse call system or bed-exit alarm.

Additional Specification for Optional Capabilities

The bulk of the previous specification was disclosed in U.S. patent application Ser. No. 13/598,568, filed Aug. 29, 2012 to Daniel Murphy. The remaining specification that follows is newly disclosed material.

Figure 3:
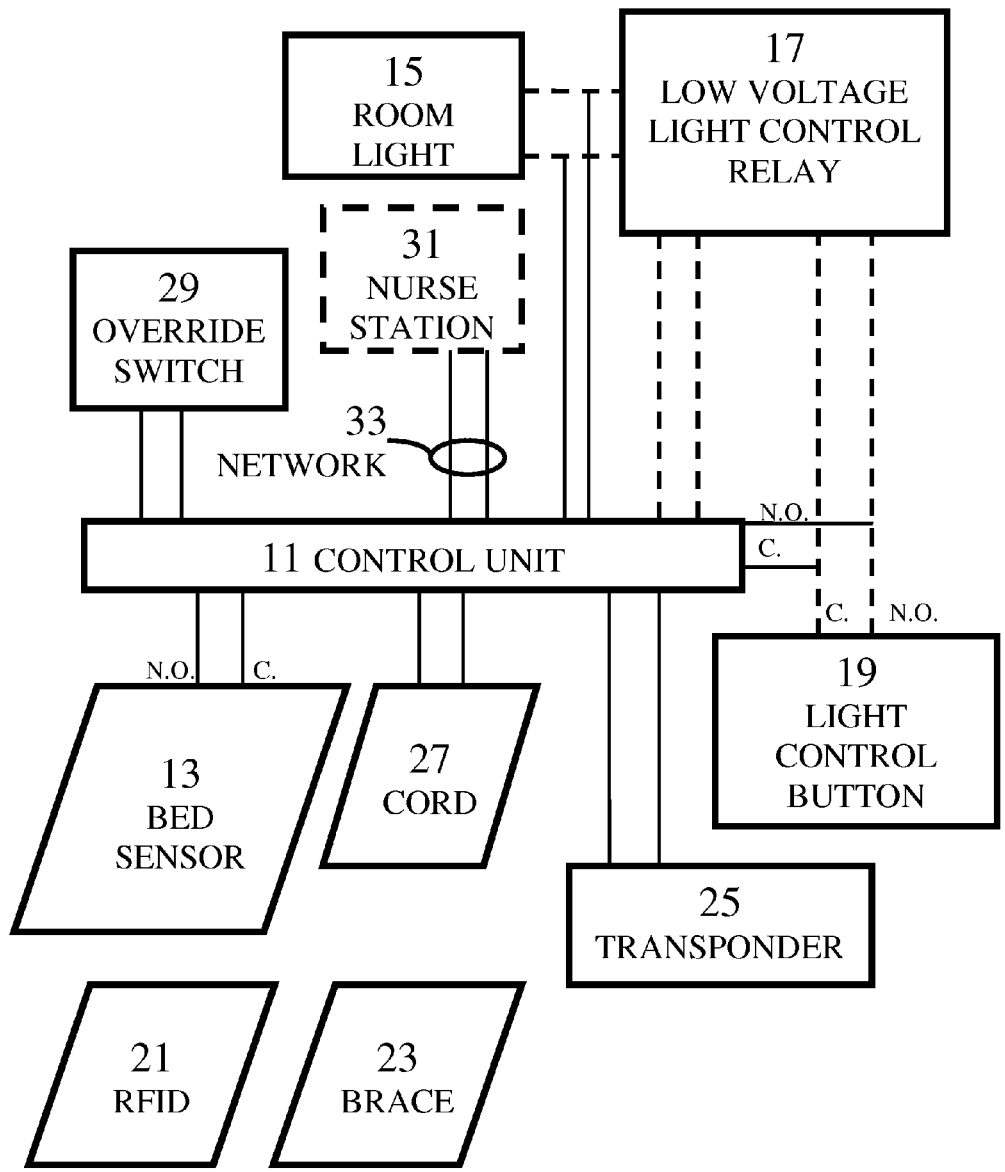
FIG. 3 is a block diagram for a second embodiment of the invention with patient locating capability, optional nurse call system, and staff-based room lighting.

As shown in FIG. 3, the optional components of the room lighting system can include a patient locating control element, optional nurse call system, and provide individualized staff-based and room lighting, and as already mentioned, a Manual Override Switch 29.

Figure 4:
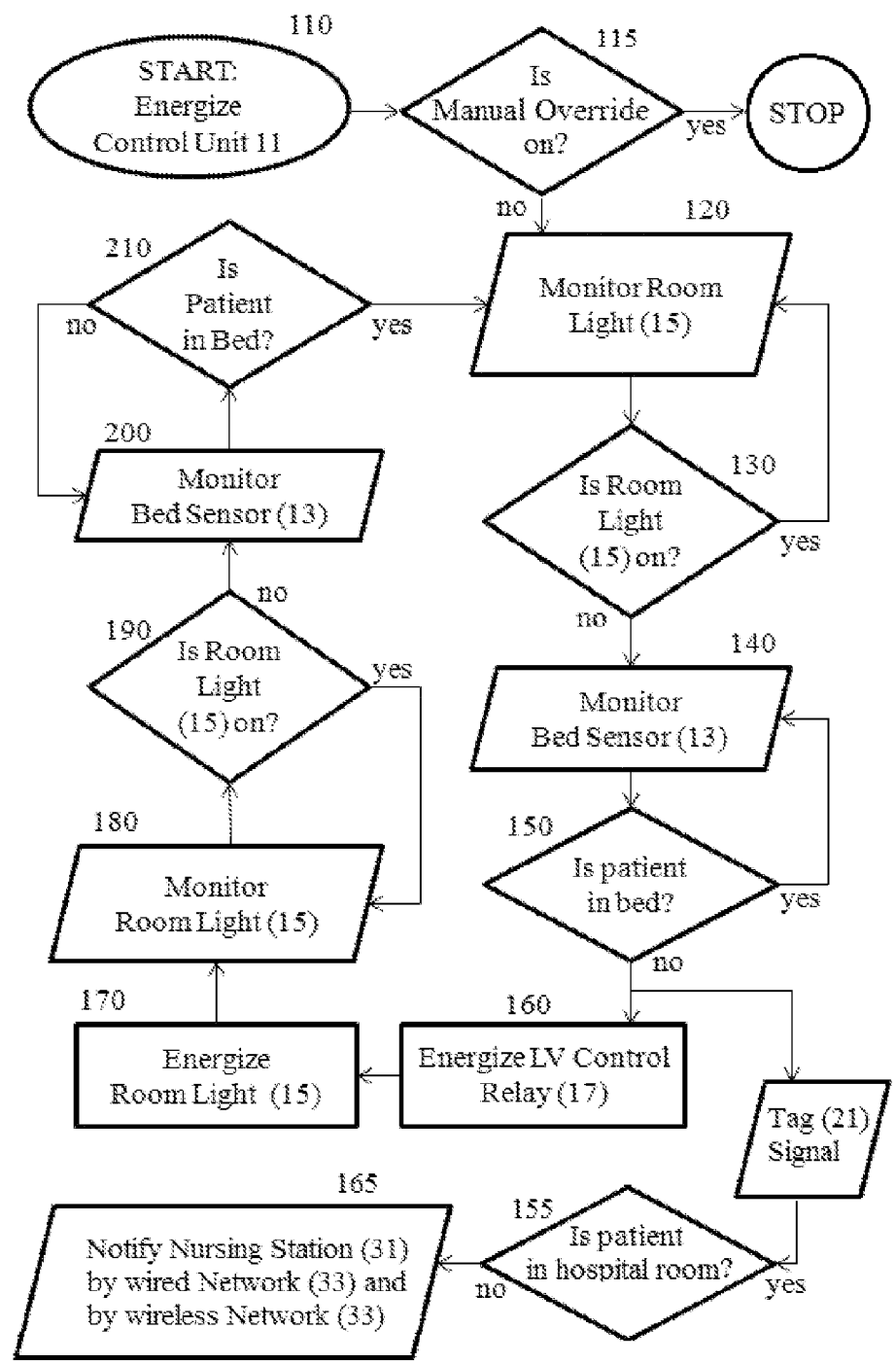
FIG. 4 is a flow chart for a second embodiment of the invention as shown in FIG. 3.

As the flow chart of FIG. 4 shows, the invention continuously monitors of the Manual Override Switch 29 (Step 115); when a user activates the Switch 29, the system ceases operation.

The patient locating control element comprises a location element used to detect whether a patient has traveled out of range of a Transponder 25 inside the patient's hospital room. FIG. 3 shows two means for determining that a patient is inside his room. One such element could be a Radio-Frequency Identification Device (RFID) Tag 21 that is affixed to a patient's badge or Bracelet 23. Another means would includes a sensor that monitors the resistance across a closed two-connector Cord 27 connected between a patient and the Control Unit 11 that or other fixed furniture. When the patient disconnects or breaks the Cord 27 from the Control Unit 11, the circuit completed by the Cord 27 is interrupted, signaling to the Control Unit that the patient is no longer in the room.

As shown on FIG. 4, once the Control Unit 11 has an indication that the patient has left his bed (Step 150), it then uses input through the Tag 21 (by means of the Transponder 25) to determine if the patient has left his room, and sends a status of this condition to the Nursing Station 31 (Steps 155, 165).

Though this embodiment of the invention alerts the Nursing Station 31 only when a patient leaves his room, the system could also be programmed to alert, track and log all bed and room entries.

As shown on FIG. 3, the Control Unit 11 can be connected to a Nurse Station 31 by one or more networking methods, indicated as Station-to-Room Network 33, which provides lighting information and allow the nurse to know if the patient in his bed. Such connection can be wired with an Ethernet connection, a wireless Wi-Fi connection, by a Zigbee circuit and protocol, or any number of other wired and wireless methods.

As a measure of redundancy for critical applications, the system can employ multiple types of networks at one time, as indicated in Step 165. This allows individuals at the Nursing Station 31 to take corrective action if one communication system has failed.

The combination of a wired and wireless means for communication between the Control Unit 11 and the Nursing Station 31 allows the Control Unit to ensure continuous connectivity between bed, Control Unit 11, and Nursing Station 31, and if not properly functioning, to alert the Station 31 wirelessly. (Note that the nursing station is not part of the invention, but an existing element with which the invention communicates. It is given nomenclature only for ease of discussion.)

As an another lighting control option, the Control Unit can take input from a Transponder 25 that communicates with staff who enter a hospital room in which it is located, activated by entering staff which carry RFID Tags 21 on their badge or bracelet. Each staff can carry a Tag 21 programmed with information regarding the level of light required for that staff member.

For example, a nurse that is simply checking the pulse of the patient needs almost no light. The nurse may choose to carry a Tag 21 that communicates with the Transponder 25 that the light need not be increased at all. The control unit takes that information, can log the presence of the nurse and convey that information to the Nursing Station 31, but leave the lighting unchanged.

However, a doctor who is examining a large area of skin on a patient may want the room lighting to be as bright as possible. Correspondingly, that doctor's Tag 21 would communicate to the Transponder 25 and Control Unit 11, and the Control Unit would raise the room lighting.

Because multiple medical staff can be in a single room, the Control Unit 11 raises the lighting in a room to reflect the Tag 21 indicating the highest level of room lighting necessary.

Thus, each RFID Tag 21 conveys a signal to the Control Unit 11, which then can light a hospital room as appropriate to that staff present in the room, based on the staff member working in the room who needs the brightest light of those present, and changes the lighting from one level to another, doing so gradually or quickly, as indicated by the Tag 21.

Another optional element is a Manual Override Switch 29 which provides staff with the ability to cease system control of room lighting. The Switch 29 can be located in the room, or just outside, or even at the Nursing Station 31.

Drawing and Specification Legend:

11—Control Unit
13—Bed Sensor
15—Room Light
17—Low Voltage Light Control Relay
19—Light Control Button
21—Radio-Freq. Ident. Device (RFID) Tag
23—Bracelet
25—Transponder
27—Cord
29—Manual Override Switch
31—Nursing Station (existing)
33—Station-to-Room Network

The invention claimed is:

1. An improved Bed-Exit Lighting System, comprising:
 a. a sensor that provides a signal to a control unit when a user leaves a bed;
 b. a room light in the same room as the bed;
 c. a means other than a photoelectric cell for detecting light in the vicinity of the bed which is connected to the control unit;
 d. a relay between the room light and a power source to the room light that connects the power source to the room light upon receiving a control signal;
 e. the control unit connected to the relay, that controls the relay so as to provide power to a room light when a user in the bed gets out of the bed when the room is dark;
 f. the control unit delays the monitoring of the bed sensor after the room light is turned off for a period of time, allowing a user to get into the monitored bed; and
 g. a transponder which detects the presence of RFID tags.

2. An improved Bed-Exit Lighting System as in claim 1, additionally comprising a means for communicating hospital room conditions to a nursing station.

3. An improved Bed-Exit Lighting System as in claim 1, additionally comprising a programmable room lighting response to the presence of RFID tags.

4. An improved Bed-Exit Lighting System as in claim 1, additionally comprising a means of communicating the movement of medical staff in or out of a hospital room.

5. An improved Bed-Exit Lighting System as in claim 1, additionally comprising a means of recording movement of medical staff in or out of a hospital room.

6. An improved Bed-Exit Lighting System as in claim 1, additionally comprising a manual override switch that causes the System to cease operation.

7. An improved Bed-Exit Lighting System as in claim 1, additionally comprising a means of logging movement of medical staff in or out of a hospital room, a manual override switch, a means of communicating with a nurse station that a patient has left his bed, and a programmed lighting response to the presence of one or more RFID tags.

8. A method of controlling room lighting a room with a bed, comprising:
   a. monitoring the room light around a target bed until the room is dark; and,
   b. monitoring a bed sensor that indicates the presence of a person in the bed; and,
   c. energizing a control relay to provide power to the room light when the bed sensor detects that a person is leaving the bed and the room is dark; and,
   d. ceasing operation once the room light is on, until the room light is turned off; and
   e. waiting a period of time before beginning to monitor the bed sensor after the light is turned off; and
   f. monitoring the bed sensor after the light is turned off; and,
   g. monitoring the presence of medical staff in the room.

9. A method of controlling room lighting as in claim 8, with the additional step of reporting room conditions to a nursing station.

10. A method of controlling room lighting as in claim 9, with the additional step of logging room conditions to a nursing station.

11. A method of controlling room lighting as in claim 9, with the additional step of logging room conditions.

12. A method of controlling room lighting as in claim 9, with the additional step of logging room conditions.

13. A method of controlling room lighting as in claim 8, in which an RFID tag system operates with a transponder to monitor the presence of medical staff in the hospital room.

14. A method of controlling room lighting as in claim 8, in which communication between the hospital room and nursing station is by use of physical wired conductors.

15. A method of controlling room lighting as in claim 8, in which communication between the hospital room and nursing station is by both physical wired conductors and a wireless network.

16. A method of controlling room lighting as in claim 8 with the additional step of continuously monitoring connectivity between the hospital room and nursing station using redundant multiple systems.

* * * * *